United States Patent [19]

Stewart et al.

[11] Patent Number: 4,923,963

[45] Date of Patent: * May 8, 1990

[54] BRADYKININ ANTAGONIST PEPTIDES

[75] Inventors: John M. Stewart; Raymond J. Vavrek, both of Denver, Colo.

[73] Assignee: Nova Technology Limited Partnership, Baltimore, Md.

[ * ] Notice: The portion of the term of this patent subsequent to Sep. 15, 2004 has been disclaimed.

[21] Appl. No.: 91,995

[22] Filed: Sep. 2, 1987

[51] Int. Cl.$^5$ .............................................. C07K 7/18
[52] U.S. Cl. ................................. 530/314; 514/803; 530/327; 530/328
[58] Field of Search ...................... 530/314, 327, 328; 514/15, 803, 14

[56] References Cited

U.S. PATENT DOCUMENTS

| | | | |
|---|---|---|---|
| 3,364,193 | 1/1968 | Hernpel et al. | 530/314 |
| 4,399,124 | 8/1983 | Fauve | 530/314 |
| 4,693,993 | 9/1987 | Stewart et al. | 530/314 |

OTHER PUBLICATIONS

Chem. Abstracts, vol. 101, 1984, 84128n.
Chem. Abstracts, vol. 103, 1985, 98853y.
Chem. Abstracts, vol. 105, 1986, 184127n.

*Primary Examiner*—Lester L. Lee
*Assistant Examiner*—Wessendorf, T. D.
*Attorney, Agent, or Firm*—Breneman & Georges

[57] ABSTRACT

The substitution of the L-Pro at the 7-position of the peptide hormone bradykinin or other substituted analogs of bradykinin with an aliphatic, cyclic or aromatic amino acid of the D-configuration converts bradykinin agonists into a bradykinin antagonist. The invention further includes additional modifications at other positions within the novel 7-position modified bradykinin antagonists including C-terminal and N-terminal extensions and replacement of arginine in the one and nine positions which increase enzyme resistance, antagonist potency and/or specificity of the new bradykinin antagonists. The analogs produced are useful in treating conditions and diseases of the mannal and human body in which an excess of bradykinin or related kinins are produced or injected as by bites into the body.

6 Claims, No Drawings

BRADYKININ ANTAGONIST PEPTIDES

BACKGROUND OF THE INVENTION

1. Cross Reference To Related Applications

The invention pertains to new and useful bradykinin antagonist peptides and is related to the subject matter of U.S. application Ser. Nos. 092,148, 092,179, and 092,192 all filed on Sept. 2, 1987.

2. Field Of The Invention

The invention relates to novel biologically active peptides which act as antagonists of the biological activities of bradykinin, their pharmaceutically acceptable salts, and their application as therapeutic agents. More particularly the invention pertains to the substitution of L-Pro at position 7 to convert bradykinin agonists into antagonists together with other modifications and substitutions at other positions including C and N-terminal extensions and modifications, amino acid deletions and the substitution of arginine in the one and nine positions of the novel bradykinin antagonists.

3. Description Of The Prior Art

In the 25 years since the sequence of the potent mammalian vasodilator peptide bradykinin was described and synthesized (Boissonnas et al., Experientia 16: 326, 1960) several hundred sequence-related peptide analogs have been synthesized and assayed in biological systems (Schroeder, in Handbook of Experimental Pharmacology, Vol. 25, (Springer Verlag) pp. 324–350, 1970) (Stewart, Handbook of Experimental Pharmacology, Vol. 25 (Supplement), (Springer Verlag) pp. 227–272, 1979). The objective in these studies was to investigate the varied physiological and pharmacological roles of bradykinin.

Bradykinin, and its physiologically important related peptides kallidin (Lys-bradykinin) and Met-Lys-bradykinin, exhibit physiological actions which qualify them as mediators of inflammatory reactions, hypotensive states, and pain. Bradykinin is overproduced in pathological conditions such as septic shock (Robinson et al., Am. J. Med. 59:61, 1975) and hemorrhagic (Hirsrh et al., J. Surg. Res. 17:147, 1974), anaphylaxis, (Collier and James, J. Physiol. 160:15P, 1966), arthritis (Jasani et al., Am. Rheum. Dis. 28:497, 1969; Hamberg et al., Agents Actions 8:50, 1978; Sharma et al., Arch. Int. Pharmacodyn 262:279, 1983), rhinitis (Proud et al., J. Clin. Invest. 72:1678, 1983; Naclerio et al., Clin. Res. 33:613A, 1985), asthma (Christiansen et al., J. Clin. Invest. 79:188–197, 1987), inflammatory bowel disease (Zeitlin and Smith, Gut 14:133–138, 1973), and certain other conditions including acute pancreatitis, post-gastrectomy dumping syndrome, carcinoid syndrome, migraine, and angioneurotic edema (Leme, Handb. Exp. Pharmacol. 50/I:464–522, 1978). The production of bradykinin from the plasma results in pain at the site of the pathological condition, and the overproduction intensifies the pain directly or via stimulation by bradykinin of the activation of the arachidonic acid pathway which produces prostaglandins and leukotrienes, the more distal and actual mediators of inflammation. Literature references describing these actions of bradykinin and related peptides are found in Handbook of Experimental Pharmacology, Vol. 25, Springer-Verlag, 1970 and Vol. 25 Supplement, 1979.

Bradykinin as discussed has been found to be produced in inflammatory reactions in the intestine provoking contraction of smooth muscle and secretion of fluid and ions. The existence of specific bradykinin receptors in the mucosal lining of the intestine and intestinal smooth muscle is demonstrated by Manning, et al in Nature (229: 256–259, 1982) showing the influence of bradykinin in very low concentrations upon fluid and ion secretion.

The production of bradykinin and associated pain in angina has been studied and reported by Kimura, et al in American Heart Journal (85: 635–647, 1973) and by Staszewska-Barczak, et al in Cardiovascular Research (10: 314–327, 1976). The reported action of bradykinin and prostaglandins acting in concert are the natural stimulus for excitation of the sensory receptors signaling the pain of myocardial ischeamia.

Bradykinin and bradykinin—related kinins are not only produced by the animal but may also be injected as a result of stings and bites. It is known that insects such as hornets and wasps inject bradykinin related peptides which also cause pain, swelling and inflammation.

The search for understanding of the mechanism of action of bradykinin, which is essential for the development of useful tools for diagnostic use, and for the development of therapeutic agents aimed at alleviating the intense pain caused by the production and overproduction of bradykinin, has been severely hindered by the lack of specific sequence-related competitive antagonists of bradykinin.

Several non-peptide, non-specific and non-selective antagonists of one or more of the biological activities of bradykinin have been described among compounds as diverse as analgesics and anti-inflammatory substances, which act via the prostaglandin system and not directly on bradykinin biological receptors (Rocha e Silva and Leme, Med. Exp, 8:287, 1963). These are antihistamines (Gecse et al, J. Pharm. Pharmacol. 21: 544, 1969); bradykinin-antibodies (Grez et al, Eu. J. Pharmacol. 29: 35, 1974); benzodiazepine derivatives (Leme and Rocha e Silva, Br. J. Pharmacol. 25: 50, 1965); high molecular weight ethylene oxide polymers (Wilkens and Back, Arch. Intl. Pharmacodynam. 209: 305, 1974); gallic acid esters (Posati et al., J. Agri. Food Chem. 18: 632, 1970) and serotonin inhibitors (Gomazkon and Shimkovich, Bull. Exptl. Biol. Med. 80: 6, 1975). None of these individual compounds or classes of compounds specifically inhibit bradykinin.

Heptyl esters of various amino acid-containing substances, such as single basic amino acids (ie. Arg and Lys) (Gecse, Adv. Exptl. Biol. Med. 70: 5, 1976), the dipeptide Phe-Gly (Gecse et al, Int. Aech. Allergy 41: 174, 1971), and of analogs of C- terminal peptide fragments of bradykinin (ie, Pro-Phe-Arg) (Claesson et al., Adv. Exptl. Med. Bicl. 120B: 691, 1979) have been reported as anti-bradykinin substances. When tested in bradykinin assay systems they prove to be weak partial agonists/antagonists, depending on the dose, with little specificity for inhibiting bradykinin action.

Preparations of damaged vascular tissue have been reported to respond to bradykinin analogs which lack the C-terminal Arg residue, but not to bradykinin itself, and analogs of these des-$Arg^9$-bradykinins have been developed as antagonists of this non-physiological activity of bradykinin. These antagonists have no significant bradykinin-like agonist effects, nor any antagonist effect on any of the physiologically significant kinin-responding systems (Regoli and Barabe, Pharmacol. Revs. 32:1,1980).

Several bradykinin analogs containing the O-methyl ether of Tyr residues at positions 5 and/or 8 have been reported to produce mixed agonist/antagonist activity on isolated uteri of galactosemic rats, but not on normal rats. The antagonism was not reliably reproducible in these animals (Stewart and Woolley, in Hypotensive Peptides, Springer Verlag, pp. 23-33, 1966).

Other changes in the bradykinin molecule have been additions of amino acids at the N-terminal end which affect the rate of enzymatic degradation of bradykinin in vivo.

The half life of bradykinin in the systemic circulation is less than 30 seconds (S. H, Ferreira & J. R. Vane, Br. J. Pharmacol. Chemotherap. 30:417, 1967). Bradykinin is completely destroyed (98-99% destruction) on a single passage through the pulmonary circulation (J. Roblero, J. W. Ryan and J. M. Stewart, Res. Commun. Pathol. Pharmacol. 6:207, 1973) as determined in the anesthetized rat by measuring the depressor effects of an agonist following intra-aortic (IA) (bypassing the pulmonary circulation) and intravenous (IV) administration. Resistance of bradykinin agonists to pulmonary kininase destruction in vivo is promoted by addition of single (i.e., DArg-, DLys-, Lys-) and double (DLys-Lys-) basic amino acid residues to the N-terminal of the bradykinin sequence. The addition of the dipeptide Lys-Lys to the N-terminal of bradykinin agonists confers complete resistance to in vivo destruction on initial passage through the pulmonary circulation (Roblero, Ryan and Stewart, Res. Comm. Pathol. Pharmacol. 6:207, 1973).

SUMMARY OF INVENTION

The invention relates to the modification of the sequence of the mammalian peptide hormone bradykinin (Arg-Pro-Pro-Gly-Phe-Ser-Pro-Phe-Arg) and pharmaceutically acceptable salts thereof, at the Pro residue at position 7 in a unique manner which, for the first time, produces sequence-related analogues that act as specific and competitive inhibitors of the biological activities of bradykinin. The invention specifically relates to the substitution of the L-Pro at position 7 with substituted and unsubstituted aromatic amino acids of the D-configuration, a change which converts bradykinin agonists into antagonists, and includes additional modifications at other positions within the 7-position modified bradykinin antagonist which confer increased antagonist potency, resistance to enzymatic degradation and/or tissue specificity on the D-amino acid-containing bradykinin sequence. The invention further includes the necessary substitution of L-Pro at position 7 with substituted and unsubstituted amino acids of the D-configuration together with the substitution of arginine in the one and nine positions with D or L-cyclic (heterocyclic or alicyclic) amino acid residue, D or L aliphatic amino acid residue or a D or L substituted or unsubstituted aromatic acid residue. The invention also includes C-terminal modifications and extensions. More specifically, the invention relates to the peptides of the general formula:

N—A1—B—C—D—W—X—Y—Z—A9—Cn     Formula I
(0    1   2  3  4   5   6   7   8   9   10)(position number)

Wherein N is a hydrogen atom or single acidic, basic or neutral aromatic amino acid residue of the D- or L-configuration, such as D-Arg, D-Lys or L-Thi, an N-terminal enzyme protecting group selected from the group comprising acyl-type protecting groups, aromatic urethane-type protecting groups, alkyl-type protecting groups, or alternately N is a di- or poly-peptide containing amino acids of the D- or L-configuration, such as Lys-Lys, Met-Lys, or Gly-Arg-Met-Lys;

A1 and A9 are either or both an Arg residue or other cyclic (heterocyclic or alicyclic) amino acid residue, aliphatic amino acid residue or an aromatic or substituted aromatic amino acid residue of the D or L configuration;

B is D- or L-pro residue, or other D- or L-cyclic (heterocyclic or alicyclic) or noncyclic aliphatic amino acid residue, such as L-hydroxyproline (Hyp), 3-4-dehydroproline (DHP) or a D or L-aromatic or substituted aromatic amino acid residue;

C is D- or L-Pro residue, or other cyclic (heterocyclic or alicylic), aliphatic, aromatic or substituted aromatic amino acid residue of the D- or L-configuration;

D is a Gly residue or other aliphatic, cyclic, aromatic or substituted aromatic amino acid residue of the D or L-configuration, such as Ala;

W is a Phe residue of the D or L-configuration, or a substituted Phe or other aliphatic or aromatic amino acid residue of the D- or L-configuration, such as Leu, beta-2-thienyl-alanine (Thi) or beta-(3-pyridyl)-alanine (Pal) or a cyclic amino acid such as a D or L-Pro residue;

X is a Ser residue of the D- or L-configuration, a Gly residue, or other D- or L-aliphatic, cyclic or aromatic or substituted aromatic amino acid residue, such as pCl-D-Phe, CDF or D-Phe;

Y is a D- aromatic amino acid residue, or substituted aromatic amino acid residue, such as D-Phe, beta-(2-thienyl)-D Ala (DThi), beta-(3-pyridyl)-D-Ala (D-Pal), β-2-naphthyl-D Ala (D-Nal), DHis, D-homo-Phe (DhPhe), O-methyl-DTyr (DOMT), D-alphaphenyl-Gly (DPhg), DTrp, DTyr or pCl-DPhe (CDF);

Z is a Phe residue of the D or L configuration, or a substituted Phe of other aliphatic or aromatic amino acid residue of the D- or L-configuration, such as Leu, Thi or Pal or a cyclic amino acid such as a D or L-Pro; and Cn is a hydroxyl group or a C-terminal extension such as an amide, alkoxy group, an acidic, basic or neutral aliphatic aromatic, or cyclic amino acid residue of the D- or L-configuration or a peptide extension composed of D- or L-amino acids.

In a preferred compound of the general formula I the substituents have the following identity: A=H or Arg B=Pro or Hyp, C=Pro or Hyp, D=Gly, W=Z=Phe or Thi, X=Ser and Y=any aromatic amino acid of the D-configuration.

Salts of peptides of general formula I include salts with HCl, TFA, AcOH, as well as other pharmaceutically acceptable salts.

The following Tables I and II show substitutions that can be made in the bradykinin polypeptide and the effect of such substitutions. Indicated substitutions of the 0, 1, 2, 3, 5, 7 and 8 amino acid residues of bradykinin yield preferred bradykinin antagonists.

TABLE I
SUBSTITUTIONS IN BRADYKININ ANTAGONISTS

```
                                          D-Pro
                                          DNal
              DHP     DHP                 DPNF
              Azt     Azt                 DPhe
              Thz     Thz                 DTyr
              Inip    Inip                DPal
              DPro    DPro                DOMT
              ΔPro    ΔPro                DThi
              Hyp     Hyp                 DAla
                              Ala
                              Sar
                                ↓
   N    A1   Pro    Pro   Gly  Phe   Ser   Pro   Phe   A9   Cn DArg        Arg          Thi       Gly        Thi       Ile—Tyr
  Lys—Lys     DArg         OMT       DPhe       OMT       DIle—Tyr
  DLys—Lys    DPhe         Pal       CDF        Pal       NH₂

Phe         Phe          CLF       DNaL       CLF
  Thi         DThi         PNF       DPal       PNF
  Ac          DPal         Nal       DThi       Nal
  DNal        DNal
              CDF
              DTyr
              FDF
              DTrp
              DVal
              DIle
              Ile
```

Thi = β-(2-Thienyl)alanine
Pal = β-(3-Pyridyl)alanine
Hyp = 4-Hydroxyproline
Azt = Azetidine-2-carboxylic acid
Thz = Thiazolidine-2-carboxylic acid
Inip = Isonipecotic acid
OMT = 0-Methyltyrosine
CDF = para-chloro-D-phenylalanine
Nal = β-(2-Naphthyl)-alanine
CLF = para-chloro-L-phenylalanine
PNF = para-nitrophenylalanine
ΔPro = 2,3-Dehydroproline
DHP = 3,4-Dehydroproline
FDf = para-fluoro-D-phenylalanine
Ac = acetyl.

TABLE II
CHARACTERISTICS OF BRADYKININ ANTAGONISTS

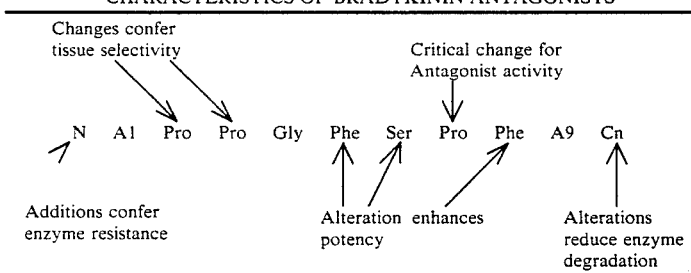

DETAILED DESCRIPTION

The synthesis of the peptides of general Formula I, including derivation, activation, and coupling of protected amino acid residues, and their purification, and the analytical methods for determining identity and purity are included in the general body of knowledge of peptide chemistry, as described in Houben Weyl "Methoden der Organischen Chemie" Vol. 16, parts I & II (1974) for solution-phase synthesis, and in "Solid Phase Peptide Synthesis" by Stewart and Young (1984) for synthesis by the solid-phase method of Merrifield.

Any chemist skilled in the art of peptide synthesis can synthesize the peptides of general Formula I by standard solution methods or by manual or automated solid-phase methods.

The symbols and abbreviations used for amino acids, their derivatives and protecting groups, and peptides and their salts are those customarily used in peptide chemistry (Biochem. J. 126:773, 1972, the Journal reference is hereby incorporated by reference). For convenience several abbreviations are defined in Table III reproduced below. All amino acid residues, except Gly, described in the specification (but not the claims which claims, unless otherwise specifically limited by the claim, cover compositions of the D- and L-configuration) are of the L-configuration unless otherwise specified.

TABLE III

| ABBREVIATIONS FOR AMINO ACID RESIDUES | |
|---|---|
| Aib | alpha-aminoisobutyric acid |
| Ala | alanine |
| Azt | azetidine-2-carboxylic acid |
| CDF | para-chloro-D-phenylalanine |
| CLF | para-chloro-L-phenylalanine |
| DHP | 3,4 dehydroproline |
| FDF | para-fluoro-D-phenylalanine |
| hPhe | homo-phenylalanine |
| His | histidine |
| Hyp | 4-hydroxy-proline |
| Gly | glycine |
| Ile | Isoleucine |
| Inip | isonipecotic acid |
| Leu | leucine |
| MDY | O-methyl-D-tyrosine |
| OMT | O-methyl-tyrosine |
| Nal | beta-(2-naphthyl)-alanine |
| ΔPro | 2,3-dehydroproline |
| Pal | beta-(3-pyridyl)-alanine |
| Phg | alpha-phenylglycine |
| Phe | phenylalanine |
| PNF | para-nitrophenalanine |
| Sar | sarcosine |
| Thi | beta-(2-thienyl)-alanine |
| Thz | thiazolidine-2-carboxylic acid |
| Tyr | tyrosine |

(all other abbreviations follow the IUPAC standards for amino acid residues)

The following examples are illustrative of compounds of this invention with general formula I and are not limitative. All percentages and ratios are by weight when solids are involved and by volume when only liquids are involved.

EXAMPLE 1

Preparation of Arg-Pro-Pro-Gly-Phe-Ser-DPhe-Phe-Arg (DPhe[7]-BK).

A mixture of 6.4 gm of tertiary butyloxy carbonyl(g-paratoluene sulfonyl)-Arg [Boc-Arg(Tos)](15 mMole) and 183 mg of N,N-dimethylaminopyridine (1.5 mMole) was dissolved in a mixture of 20 ml of dimethylformamide (DMF) and 125 ml of dichloromethane (DCM). Fifteen g (grams) of hydroxymethyl-polystyrene-divinyl benzene (1% crosslinked, containing 0.74 mMole of free hydroxyl group per g of resin) was added, followed by 60 ml of a 0.25M solution of dicyclohexylcarbodiimide (DCC) in DCM at room temperature. The suspension was stirred at room temperature overnight, filtered, and the resin was washed three times with 60 ml of DCM, three times with 60 ml of methyl alcohol (MeOH), and reswollen in 120 ml of DCM. The coupling of another portion of Boc-Arg(Tos) was conducted on the resin as above. After filtering and washing the resin it was reswollen in 120 ml of DCM, and 2.1 ml of benzoyl chloride and 1.5 ml of triethylamine (Et$_3$N) were added. After stirring the suspension for 30 minutes at room temperature the resin was filtered, washed three times with 60 ml portions of DCM MeOH, washed three times with 60 ml portion of MeOH and finally washed three times with 60 ml portions of DCM. The resin was air dried to constant weight to give 18.5 gm of Boc-Arg(Tos)-hydroxymethyl-resin, with an actual amino acid content of 0.272 millimoles of Arg per g of resin as determined by quantitative amino acid analysis of a sample of the amino acid resin following hydrolysis (4 hr, 130 degrees C.) in 6N HCL/propionic acid.

The resin, 1.5 gm containing a total of 0.4 mMole of Arg, was placed in the reaction vessel of an automatic solid-phase synthesizer (Beckman model 990) and subjected to one cycle of addition for the coupling of Boc-Phe as follows;

PROGRAM A. STANDARD DCC COUPLING

The resin was washed three times with 20 ml portions of DCM. The resin was then equilibrated with 20 ml of a 1:3 ratio of trifluoroacetic acid (TFA) in DCM containing 0.1% indole for 1.5 minutes. The equilibration was then repeated for 30 minutes. The resin was then washed six times with 20 ml portions of DCM followed by neutralization with a 10% solution of (Et$_3$N) in DCM for one and one half minutes, then the neutralization step was repeated. The resin was washed six times with 20 ml of DCM and then equilibrated with a solution of 1.0 mMole of Boc-Phe in DCM for one and one half minutes. Then four ml of 0.25N DCC in DCM was added and the mixture stirred for two hours. Then the resin was washed three times with 20 ml portions of DCM.

A second cycle of addition was performed according to Program B:

PROGRAM B. REVERSE ADDITION

The procedure of Program A through neutralization and following washes was repeated. Then 1.0 mMole of DCC in 4 ml of DCM was added and the resin and solution were mixed for one and one-half minutes. Then 1.0 mMole of Boc-D-Phe in 12 ml DCM was added and the resin and solution were mixed for two hours. The resin was then washed six times with 20 ml portions of DCM.

The N-Terminal protecting group was removed according to the following sequence:

PROGRAM C. TERMINAL DEPROTECTION

The procedure of PROGRAM A up to the neutralization with triethylamine was repeated. The resin was then washed 6 times with 20 ml portions of ethyl alcohol and the peptide-resin was air dried giving 1.66 gm of DPhe-Phe-Arg-Resin as the trifluoroacetic acid salt.

Synthesis was continued with 410 mg of the DPhe-Phe-Arg-Resin TFA salt. The next residue was added according to PROGRAM D.

PROGRAM D. RECOUPLE

The peptide-resin salt was first washed three times with 20 ml portion of DCM, then neutralized with 10% Et$_3$N DCM for 1.5 minutes. The neutralization step was then repeated and the peptide-resin-salt was washed six times with 20 ml portions of DCM. The peptide-resin was then equilibrated with a solution of 1.0 mMole of Boc-Ser(OBzl) in DMF for 1.5 minutes. Four ml of 0.25N DCC in DCM was added and mixed with the resin for two hours. The product was washed three times with DCM.

The following amino acid derivatives were added to the growing peptide chain according to the listed Programs: Boc-Phe (A), Boc-Gly (A), Boc-Pro (A), Boc-Pro (A), followed by recouple of Boc-Pro (D), Boc-Arg(Tos)(dissolved in 2 ml DMF+9 ml DCM), (A), followed by Program C. This gave 530 mg of protected nonapeptide-resin as the TFA salt.

A 510 mg portion of the peptide-resin above was suspended in 10 ml of liquid anhydrous HF containing 1 ml of anisole at −70 degrees C. and stirred 45 min. at 0 degrees C. HF and anisole were removed by vacuum (1 hr water pump, 1 hr vacuum pump), the peptide plus resin was washed three times with 20 ml portions of ethyl ether (Et$_2$O) and the peptide extracted into glacial acetic acid using three 6 ml extractions. The acetic acid solution was lyophilized to give 185 mg of crude deprotected peptide.

The peptide was purified by countercurrent distribution (CCD) (100 upper phase transfers in a Post CCD apparatus) in the solvent system nBuOH:1% TFA (1:1). The content of the tubes corresponding to the main peptide-containing peak, as determined by the quantitative Sakaguchi reagent, was collected, the solvent evaporated under reduced pressure, the residue dissolved in glacial acetic acid (AcOH) and lyophilized to give 140 mg of peptide with a partition coefficient (k) from the CCD of 5.7. Repeating the countercurrent distribution in the solvent system n:BuOH:AcOH:H$_2$O (4:1:5) gave, upon detection and workup as described above, 73 mg of Arg-Pro-Pro-Gly-Phe-Ser-DPhe-Phe-Arg as the TFA salt (k=0.2). Thin layer chromatographs (TLC) on Merck glass precoated silica gel plates in the solvent systems nBuOH:AcOH:H$_2$O (8:3:4) and EtOAc:-pyridine:AcOH:H$_2$O (5:5:1:3) gave Rf(834) of 0.17 and Rf(5513) of 0.36 for the pure peptide, as visualized by the chlorine-tolidine peptide identification spray. Quantitative amino acid analysis (Beckman 120 instrument) after acid hydrolysis (17 hr in sealed glass vials under N$_2$ at 110° C. in 2 ml 6N HCl containing 2 drops 2-mercaptoethanol and 40 microliters of phenol gave the following ratios of amino acids: Arg(2.12); Pro(1.93); Gly(1.01); Phe(2.98); Ser(0.96).

EXAMPLES 2–40

Examples 2–40 represent bradykinin antagonists containing a hydrophobic amino acid residue at positions one and seven and were prepared by methods similar to those described in Example 1 and are not limitative.

2. CDF-Pro-Pro-Gly-Phe-Ser-DPhe-Phe-Arg (CDF$^1$DPhe$^7$-BK): k(415)=2.57 Arg - 1.03, Pro - 1.95, Gly - 1.04, Phe - 2.98, Ser - 0.94, CDF - 1.06.

3. CDF-Pro-Hyp-Gly-Phe-Ser-DPhe-Phe-Arg (CDF$^1$Hyp$^3$DPhe$^7$-BK): k(415)=1.947 Arg - 1.05, Pro - 1.00, Gly - 0:96, Phe - 3.02, Ser - 0.94, CDF - 1.10, Hyp - 0.99.

4. DArg-CDF-Pro-Pro-Gly-Phe-Ser-DPhe-Phe-Arg (DArg$^0$CDF$^1$ -DPhe$^7$-BK): k(415)=0.754.

5. DArg-CDF-Pro-Hyp-Gly-Phe-Ser-DPhe-Phe-Arg (DArg$^0$CDF$^1$Hyp$^3$DPhe$^7$-BK): k(415)=1.272 Arg - 1.92, Pro - 1.03, Gly - 1.05, phe - 3.04, Ser - 0.95, CDF - 1.00, Hyp - 1.00.

6. CDF-Pro-Pro-Gly-Phe-Ser-DThi-Phe-Arg (CDF$^1$DThi$^7$-BK): k(415) =0.460 Arg - 1.08, Pro - 2.01, Gly - 1.03, Phe - 2.00, Ser 0.91, Thi - 0.93, CDF - 1.03.

7. DArg-CDF-Pro-Pro-Gly-Phe-Ser-DThi-Phe-Arg (DArg$^0$CDF$^1$ DThi$^7$-BK): k(415)=0.754 Arg - 2.09, Pro - 1.92, Gly - 1.03, Ph - 2.10, Ser - 0.92, Thi - 0.91, CDF - 1.09.

8. DArg-Pro-Hyp-Gly-Thi-Ser-DPhe-Thi-Arg (DArg$^1$Hyp$^3$ Thi$^{5,8}$DPhe$^7$-BK): k(1.1)=2.279 Arg - 2.11, Pro - 1.04, Gly - 1.03, Phe - 1.13, Ser - 0.75, Hyp - 1 55, Thi - 1.90.

9. DTyr-Pro-Hyp-Gly-Phe-Ser-DPhe-Phe-Arg (DTyr$^1$Hyp$^3$ DPhe$^7$-BK): k(415)=1.326 Arg - 0.99, Pro - 1.06, Gly - 1.02, Phe - 3.02, Tyr - 1.01, Ser - 0.94, Hyp - 0.96.

10. DArg-DTyr-Pro-Hyp-Gly-Phe-Ser-DPhe-Phe-Arg (DArg$^0$DTyr$^1$ Hyp$^3$DPhe$^7$-BK): k(415)=0.408 Arg - 2.06, Pro - 1.06, Gly - 1.04, Phe - 3.19, Ser - 0.88, Hyp - 0.92, Tyr - 0.85.

11. FDF-Pro-Hyp-Gly-Phe-Ser-DPhe-Phe-Arg (FDF$^1$Hyp$^3$DPhe$^7$-BK): k(415)=1.857 Arg - 1 00, Pro - 1.03, Gly - 1.05, Phe - 2.99, Ser - 0.93, FDF - 0.95, Hyp - 1.05.

12. DArg-FDF-Pro-Hyp-Gly-Phe-Ser-DPhe-Phe-Arg (DArg$^0$FDF$^1$ Hyp$^3$DPhe$^7$-BK): k(415)=0.538 Arg - 2.11, Pro - 1.02, Gly - 1.05, Phe - 2.96, Ser - 0.88, Hyp - 0.94, FDF - 1.04.

13. DTrp-Pro-Hyp-Gly-Phe-Ser-DPhe-Phe-Arg (DTrp$^1$Hyp$^3$ DPhe$^7$-BK): k(415)=8.091.

14. DArg-DTrp-Pro-Hyp-Gly-Phe-Ser-DPhe-Phe-Arg (DArg$^0$DTrp$^1$ Hyp$^3$DPhe$^7$-BK): k(415)=7.333.

15. DVal-Pro-Hyp-Gly-Phe-Ser-DPhe-Phe-Arg (DVal$^1$Hyp$^3$ DPhe$^7$-BK) k(415)=0.754 Arg - 1.02, Pro - 0.95, Gly - 1.06, phe - 3.18, Ser - 0.91, Hyp - 0.98, Val - 0.90.

16. DArg-DVal-Pro-Hyp-Gly-Phe-Ser-DPhe-Phe-Arg (DArg$^0$DVal$^1$ Hyp$^3$DPhe$^7$-BK): k(415)=0.370 Arg - 2.06, Pro - 0.94, Gly - 0.99, Phe - 3.01, Ser - 0.95, Hyp - 1.02, Val - 1.01.

17. DIle-Pro-Hyp-Gly-Phe-Ser-DPhe-Phe-Arg (DIle$^1$Hyp$^3$ DPhe$^7$-BK): k(415)=1.128 Arg - 1.01, Pro - 0.96, Gly - 0.97, Phe - 3.03, Ser - 0.98, Hyp - 1.03, Ile - 0.98.

18. DArg-DIle-Pro-Hyp-Gly-Phe-Ser-DPhe-Phe-Arg (DArg$^0$DIle$^1$ Hyp$^3$DPhe$^7$-BK): k(415)=0.639 Arg - 2.00, Pro - 0.92, Gly - 1.01, Phe - 3.09, Ser - 0.98, Hyp - 1.01, Ile - 0.90.

EXAMPLES 19–40

Examples 19–40 represent bradykinin antagonists containing hydrophobic amino acid residues at positions one and seven and were prepared by methods similar to those described in Example 1 and are not limitative.

19. DPhe-Pro-Pro-Gly-Thi-Ser-DPhe-Thi-Arg (DPhe$^1$Thi$^{5,8}$ DPhe$^7$-BK): k(415)=1.703 Arg - 1.05, Pro - 2 00, Gly - 1.04, Phe - 2.09, Thi - 1.91, Ser - 0.92.

20. DThi-Pro-Pro-Gly-Thi-Ser-DPhe-Thi-Arg (DThi$^1$Thi$^{5,8}$ DPhe$^7$-BK): k(415)=1.326 Arg - 1.08, Pro - 2.04, Gly - 1.02, Ser - 0.98, Phe - 1.01, Thi - 2.88.

21. DPal Pro-Pro-Gly-Thi-Ser-DPhe-Thi-Arg (DPal$^1$Thi$^{5,8}$ DPhe$^7$-BK): k(1.1)=2.333 Arg - 1.06, Pro - 2.01, Gly - 1.05, Phe 1.02, Ser - 0.96, Thi - 1.96, Pal - 0.99.

22. DNal-Pro-Pro-Gly-Thi-Ser-DPhe-Thi-Arg (DNal$^1$Thi$^{5,8}$ DPhe$^7$-BK): k(415)=3.167 Arg - 0.97, Pro - 2.09, Gly - 1.01, Phe - 1.02, Ser - 1.00, Thi - 1.89, Nal - 0.99.

23. DArg-DNal-Pro-Pro-Gly-Thi-Ser-DPhe-Thi-Arg (DArg$^0$DNal$^1$ Thi$^{5,8}$DPhe$^7$-BK): k(415)=1.273 Arg - 2.16, Pro - 2.01, Gly - 1.05, Phe - 1.01, Thi - 1.88, Nal - 0.95, Ser - 0.94.

24. Lys-Lys-DNal-Pro-Pro-Gly-Thi-Ser-DPhe-Thi-Arg (Lys-Lys-DNal$^1$Thi$^{5,8}$DPhe$^7$-BK): k(415)=0.190 Arg - 1.05, Lys - 2.13, Pro - 1.97, Phe - 0.98, Ser - 0.86, Gly - 1.01, Thi - 1.98, Nal - 1.00.

25. DNal-DNal-Pro-Pro-Gly-Thi-Ser-DPhe-Thi-Arg (DNal$^{0,1}$Thi$^{5,8}$ DPhe$^7$-BK): k(415)=7.333 Arg - 1.14, Pro - 1.90, Gly - 1.11, Phe - 1.08, Ser - 1.01, Thi - 1.93, Nal - 1.63.

26. DNal-Hyp-Hyp-Gly-Thi-Ser-DPhe-Thi-Arg (DNal$^1$Hyp$^{2,3}$ Thi$^{5,8}$DPhe$^7$-BK): k(415)=1.941 Arg - 1.10, Gly - 1.00, Phe - 0.99, Ser - 1.00, Thi- 1.94, Hyp - 1.89, Nal - 1.00.

27. DArg-DNal-Hyp-Hyp-Gly-Thi-Ser-DPhe-Thi-Arg (DArg$^0$DNal$^1$ Hyp$^{2,3}$Thi$^{5,8}$DPhe$^7$-BK): k(415)=0.587 Arg - 1.99, Gly - 1.08, Ser - 0.99, Phe - 1.04, Thi - 1.99, Hyp - 1.89, Nal - 1.02.

28. Lys-Lys-DNal-Hyp-Hyp-Gly-Thi-Ser-DPhe-Thi-Arg (Lys-Lys-DNal$^1$Hyp$^{2,3}$Thi$^{5,8}$DPhe$^7$-BK): k(415)=0.587 Arg - 1.99, Gly - 1.08, Ser - 0.99, Phe - 1.04, Thi - 1.99, Hyp - 1.89, Nal - 1.02.

29. DNal-Pro-Pro-Gly-Phe-Ser-DPhe-Phe-Arg (DNal$^1$DPhe$^7$-BK): k(415)=3.000 Arg - 1.00, Nal - 0.86, Pro - 1.93, Gly - 1.14, Phe - 3.13, Ser - 0.95.

30. DNal-Pro-Hyp-Gly-Phe-Ser-DPhe-Phe-Arg (DNal$^1$Hyp$^3$DPhe$^7$-BK): k(415)=2.448 Arg - 1.07, Pro - 1.02, Gly - 1.07, Phe - 3.01, Ser - 0.95, Nal - 0.93.

31. DArg-DNal-Pro-Pro-Gly-Phe-Ser-DPhe-Phe-Arg (DArg$^0$DNal$^1$ DPhe$^7$-BK): k(415)=1.128 Arg - 2.15, Pro - 1.95, Gly - 1.01, Phe - 3.01, Ser - 0.92, Nal - 0.96.

32. DArg-DNal-Pro-Hyp-Gly-Phe-Ser-DPhe-Phe-Arg (DArg$^0$DNal$^1$Hyp$^3$DPhe$^7$-BK): k(415)=0.786 Arg - 2.08, Nal - 0.89, Pro - 0.97, Gly - 1.02, Phe 3.16, Ser - 0.92, Hyp - 0.96.

33. DThi-Pro-Pro-Gly-Phe-Ser-DThi-Phe-Arg (DThi$^{1,7}$-BK): k(415)=1.70, Arg - 1.05, Pro - 2.07, Gly - 1.05, Phe - 2.05, Ser - 0.94, Thi - 1.84.

34. DThi Pro-Hyp-Gly-Phe-Ser-DThi-Phe-Arg (DThi$^{1,7}$Hyp$^3$-BK): k(415)=1.22 Arg 0.97, Pro - 1.07, Gly - 0.95, Phe - 2.07, Ser - 0.98, Thi - 1.85, Hyp - 1.11.

35. DArg-DThi-Pro-Pro-Gly-Phe-Ser-DThi-Phe-Arg (DArg$^0$Dthi$^{1,7}$-BK): k(415)=0.449 Arg - 1.87, Pro - 1.87, Gly - 0.98, Phe - 2.19, Ser - 0.89, Thi - 1.89.

36. DArg-DThi-Pro-Hyp-Gly-Phe-Ser-DThi-Phe-Arg (DArg$^0$DThi$^{1,7}$Hyp$^3$-BK): k(415)=0.449 Arg - 1.99, Pro - 1.06, Gly - 1.07, Phe - 2.03, Ser - 0.95, Thi - 1.82, Hyp - 1.07.

37. DNal-Pro-Pro-Gly-Phe-Ser-DThi-Phe-Arg (DNal$^1$DThi$^7$-BK): k(415)=3.00 Arg - 0.92, Pro - 2.08, Gly - 1.06, Phe - 2.05, Ser - 0.91, Thi - 1 00. Nal - 0.92.

38. DNal-Pro-Hyp-Gly-Phe-Ser-DThi-Phe-Arg (DNal$^1$Hyp$^3$DThi$^7$-BK): k(415)=2.448 Arg - 1.10, Pro - 1.05, Gly - 1.05, Phe - 2.13, Ser - 0.84, Hyp - 1.00, Thi - 0.8, Nal - 0.87.

39. DArg-DNal-Pro-Pro-Gly-Phe-Ser-DThi-Phe-Arg (DArg$^0$DNal$^1$ DThi$^7$-BK): k(415)=0.887 Arg - 2.15, Nal - 0.96, Pro - 2.00, Gly - 1.02, Phe - 2.04, Ser - 0.93, Thi - 0.90.

40. DArg-DNal-Pro-Hyp-Gly-Phe-Ser-DThi-Phe-Arg (DArg$^0$DNal$^1$Hyp$^3$ DThi$^7$-BK): k(415)=1.272 Arg - 2.16, Nal - 1.02, Pro - 0.94, Gly - 1.06, Phe - 1.99, Ser - 0.91, Thi - 1.01.

EXAMPLES 41-79

Examples 41-79 represent bradykinin antagonist peptides possessing C-terminal modifications and extensions in which arginine in position 9 has been replaced or in which an extension has been made to the C-terminal position. The compounds of Examples 41-79, unless otherwise noted were prepared by methods similar to those described in (Example 1 and are not limitative.

41. Arg-Pro-Pro-Gly-Thi-Ser-DPhe-Thi-DArg (Thi$^{5,8}$DPhe$^7$DArg$^9$ -BK): k(415)=0.266 Arg - 2.08, Pro - 2.00, Gly - 1.01, Phe -1.01, Ser - 0.94, Thi - 1.96.

42. Ac-Arg-Pro-Pro-Gly-Thi-Ser-DPhe$^7$-Thi-DArg (Ac-Thi$^{5,8}$DPheDArg$^9$-BK): k(415)=0.754 Arg - 2.09, Pro - 2.03, Gly -1.03, Phe - 0.96, Ser - 0.96, Thi - 1.93.

43. DArg-Arg-Pro-Pro-Gly-Thi-Ser-DPhe-Thi-DArg (DArg$^0$Thi$^{5,8}$ DPhe$^7$DArg$^9$-BK): k(1.1)=2.226 Arg - 3.05, Pro - 2.01, Gly -1.08, Phe - 0.94, Ser - 1.00, Thi - 1.93.

44. Lys-Lys-Arg-Pro-Pro-Gly-Thi-Ser-DPhe-Thi-DArg (Lys-Lys-Thi$^{5,8}$DPhe$^7$DArg$^9$-BK): k(1.1)=0.282 Arg - 2.00, Lys - 2.00, Pro - 1.98, Gly - 1.07, Phe - 1.03, Ser - 1.01, Thi - 1.92.

Examples 45-51 represent bradykinin antagonist peptides possessing a C-terminal phenylalanine (Phe). Peptide analogs possessing a C-terminal Phe residue are prepared by methods described in the Example 1 for the preparation of [DPhe$^7$]-BK, except that the starting amino acid resin is Boc-Phe -hydroxymethyl-Resin (Boc-Phe-HMR), which is prepared similarly to Boc-Arg(Tos)-HMR above. Boc-Phe (1.325 g (5 mMole) and 61 mg (0.5 mMole) p-dimethylaminopyridine (DMAP) are added to 5.0 g hydroxymethyl-polystyrene-divinylbenzene (2% crosslinked) in 80 ml DCM. To this is added 5 ml of 1.0M DCC in CHCl$_3$, and the mixture is stirred 3.5 hr. The mixture is filtered and the amino acid resin is washed thoroughly with DCM, EtOH, and DCM, suspended in 80 ml DCM at 0 degrees, and treated with a mixture of 4.4 ml benzoyl chloride (37.5 mM) and 3.8 ml pyridine (47 mM) for 15 min., followed by 5 hr. stirring at room temperature. The resin is filtered, washed with DCM and air dried to give 5.5 g Boc-Phe-HMR, containing 0.485 mMole of Phe per gram of resin, as determined by quantitative amino acid analysis.

45. Arg-Pro-Hyp-Gly-Phe-Ser-DPhe-Phe-Phe (Hyp$^3$DPhe$^7$Phe$^9$-BK): k(415)=1.50 Arg - 1.03, Pro - 0.96, Gly - 1.07, Phe - 3.96, Ser - 0.97, Hyp - 1.00.

46. DArg-Arg-Pro-Hyp-Gly-Phe-Ser-DPhe-Phe-Phe (DArg$^0$-Hyp$^3$DPhe$^7$Phe$^9$-BK): k(415)−0.429 Arg - 2.01, Pro - 0.99, Gly - 0.98, Phe - 3.89, Ser - 0.99, Hyp -.

47. DNal-Pro-Hyp-Gly-Phe-Ser-DPhe-Phe-Phe (DNal$^1$Hyp$^3$DPhe$^7$Phe$^9$-BK): k1.

48. DArg-DNal-Pro-Hyp-Gly-Phe-Ser-DPhe-Phe-Phe (DArg$^0$ DNal$^1$Hyp$^3$DPhe$^7$Phe$^9$-BK): k(415)=5.667.

49. DArg-Pro-Hyp-Gly-Phe-Ser-DPhe-Phe-Phe (DArg$^1$Hyp$^3$DPhe$^7$Phe$^9$-BK): k(415)=1.439 Arg - 1.04, Pro - 1.00, Gly - 1.07, Phe - 3.90, Ser - 0.94, Hyp - 1.04.

50. DArg-DArg-Pro-Hyp-Gly-Phe-Ser-DPhe-Phe-Phe (DArg$^{0,1}$Hyp$^3$DPhe$^7$Phe$^9$-BK): k(415)=0.493 Arg - 2.07, Pro - 0.95, Gly - 1.01, Phe - 4.02, Ser - 0.90, Hyp -.

The C-terminal peptide amides of Examples 51-58 were prepared employing the following procedures. In the reaction vessel of an automatic peptide synthesizer (Beckmann 990), or by manual solid phase methods, 5.0 g of commercial p-methyl-benzhydrylamine-polystyrene-divinylbenzene resin (MBHA-Resin), 1% crosslinked, is subjected to 3×1.5 min. washes with dichloromethane (DCM), 2×1.5 min. treatments with 10% Et$_3$N in DCM and 6×1.5 min. washes with DCM. The resin is equilibrated with a solution of 2.15 g (5 mMole) of commercial Boc-Arg(Tos)-OH in DCM for 1.5 min., 20 ml of 0.25M dicyclohexylcarbodiimide (DCC) in DCM is added and the mixture stirred at room temp. 2 hr. The amino acid-Resin is washed 6×1.5 min. with DCM, and stirred for 2 hr. with a mixture of 0.94 ml acetic anhydride and 1.40 ml Et$_3$N in DMF. The mixture is filtered, washed 3×1.5 min. with DCM and air dried to give 6.68 g Boc-Arg(Tos)-MBHA-Resin containing 0.404 Mmole of Arg per gram of resin, as determined by quantitative amino acid analysis on an aliquot.

The Boc-Arg(Tos)-MBHA-Resin is treated to cycles of amino acid addition with various protected amino acids by standard solid-phase methods as described in Example 1 to produce the peptide amide-Resins desired. The desired peptide amide is obtained following hydrogen fluoride cleavage of the peptide from the resin and purification as described in Example 1.

51. Arg-Pro-Pro-Gly-Thi-Ser-DPhe-Thi-Arg-NH$_2$ [(Thi$^{5,8}$DPhe$^7$-BK)-NH$_2$]: k(415)=0.149 Arg - 2.10, Pro - 1.91, Gly - 1.04, Phe - 1.04, Ser - 0.97, Thi - 1.94.

52. Ac-Arg-Pro-Pro-Gly-Thi-Ser-DPhe-Thi-Arg-NH$_2$ [(Ac-Thi$^{5,8}$DPhe$^7$-BK)-NH$_2$]: k(415)=0.515 Arg - 1.97, Pro - 1.95, Gly - 1.00, Phe - 1.02, Ser - 0.97, Thi - 2.00.

53. DArg-Arg-Pro-Pro-Gly-Thi-Ser-DPhe-Thi-Arg-NH$_2$ [(DArg$^0$ Thi$^{5,8}$DPhe$^7$-BK)-NH$_2$]: k(1.1)=1.222 Arg - 3.16, Pro - 1.94, Gly - 1.02, Phe - 1.00, Ser - 0.91, Thi - 1.97.

54. Lys-Lys-Arg-Pro-Pro-Gly-Thi-Ser-DPhe-Thi-Arg-NH$_2$ [(Lys-Lys-Thi$^{5,8}$DPhe$^7$-BK)-NH$_2$]: k(1.1)=0.220 Arg - 2.09, Lys - 2.11, Pro - 1.92, Gly - 1.01, Phe - 1.00, Ser - 0.92, Thi - 1.93.

55. Arg-Pro-Pro-Gly-Thi-Ser-DPhe-Thi-DArg-NH$_2$ [(Thi$^{5,8}$DPhe$^7$DArg$^9$-BK)-NH$_2$]: k(415)=0.191 Arg - 2.05, Pro - 1.95, Gly - 1.04, Phe - 1.05, Ser - 0.95, Thi - 1.95.

56. Ac-Arg-Pro-Pro-Gly-Thi-Ser-DPhe-Thi-DArg-NH$_2$ [(Ac-Thi$^{5,8}$DPhe$^7$DArg$^9$-BK): k(415)=0.567 Arg - 2.05, Pro - 2.04, Gly - 1.01, Phe - 1.00, Ser - 0.94, Thi - 1.97.

57. DArg-Arg-Pro-Pro-Gly-Thi-Ser-DPhe-Thi-DArf-NH$_2$ [(DArg$^0$Thi$^{5,8}$DPhe$^7$DArg$^9$-BK)-NH$_2$]: k(1.1)=1.174 Arg - 3.19, Pro - 1.94, Gly - 1.01, Phe - 0.98, Ser - 0.93, Thi - 1.95.

58. Lys-Lys-Arg-Pro-Pro-Gly-Thi-Ser-DPhe-Thi-DArg-NH$_2$ [(Lys-Lys-Thi$^{5,8}$DPhe$^7$DArg$^9$-BK)-NH$_2$]: k(1.1)=0.205 Arg - 1.95, Lys - 2.00, Pro - 2.00, Gly - 1.04, Phe - 1.01, Ser - 1.05, Thi - 1.95.

Examples 59–78 represent bradykinin antagonist peptides possessing a C-terminal amino acid and peptide extension.

59. Arg-Pro-Pro-Gly-Phe-Ser-Pro-Phe-Arg-Ile-Tyr [(BK)-Ile-Tyr]: k(415)=0.493 Arg - 1.82, Pro - 3.13, Gly - 1.15, Phe - 1.99, Ser - 1.05, Ile - 0.86, Tyr - 1.00.

60. DArg-Arg-Pro-Pro-Gly-Phe-Ser-Pro-Phe-Arg-Ile-Tyr [(DArg$^0$-BK)-Ile-Tyr]: k(415)=0.176 Arg - 2.87, Pro - 3.06, Gly - 1.12, Phe - 1.97, Ser - 1.08, Ile - 2.84, Tyr - 0.90.

61. Lys-Lys-Arg-Pro-Pro-Gly-Phe-Ser-Pro-Phe-Arg-Ile-Tyr [(Lys-Lys-BK)-Ile-Tyr]: k(1.1)=1.439 Arg - 1.96, Lys - 2.24, Pro - 3.01, Phe - 2.04, Gly - 1.01, Ser - 0.96, Ile - 0.85, Tyr - 0.93.

62. DLys-Lys-Arg-Pro-Pro-Gly-Phe-Ser-Pro-Arg-Ile-Tyr [(DLys-Lys-BK)-Ile-Tyr]: k(1.1)=1.439 Arg - 2.04, Lys - 2.05, Pro - 3.06, Phe - 2.08, Ser - 0.92, Gly - 1.05, Ile - 0.84, Tyr - 0.95.

63. Arg-Pro-Pro-Gly-Phe-Ser-DPhe-Phe-Arg-Ile-Tyr [(DPhe$^7$-BK-Ile-Tyr]: k(415)=0.639 Arg - 2.07, Pro - 2.00, Gly - 1.04, Phe - 3.05, Ser - 0.93, Ile - 0.93, Tyr - 0.98.

64. DArg-Arg-Pro-Pro-Gly-Phe-Ser-DPhe-Phe-Arg-Ile-Tyr [(DArg$^0$DPhe$^7$-BK)-Ile-Tyr]: k(415)=0.220 Arg - 2.80, Pro - 2.09, Gly - 1.17, Phe - 3.15, Ser - 0.96, Ile - 0.88, Tyr - 0.95.

65. Arg-Pro-Pro-Gly-Thi-Ser-DPhe-Thi-Arg-Ile-Tyr [(Thi$^{5,8}$DPhe$^7$-BK)-Ile-Tyr]: k(415)=0.613 Arg - 2.06, Pro - 2.04, Gly - 1.12, Phe - 1.00, Ser - 0.95, Thi - 1.99, Ile - 0.90, Tyr - 0.94.

66. DArg-Arg-Pro-Pro-Gly-Thi-Ser-DPhe-Thi-Arg-Ile-Tyr [(DArg$^0$ Thi$^{5,8}$DPhe$^7$-BK)-Ile-Tyr]: k(415)=0.235 Arg - 3.10, Pro 1.98, Gly - 1.10, Thi - 1.87, Ser - 1.00, Ile - 0.88, Tyr 1.05.

67. Arg-Pro-Hyp-Gly-Thi-Ser-DPhe-Thi-Arg-Ile-Tyr [(Hyp$^3$Thi$^{5,8}$DPhe$^7$-BK)-Ile-Tyr]: k(415)=0.493 Arg - 2.05, Pro 1.12, Gly - 1.08, Phe - 0, Thi - 1.86, Ser - 1.05, Hyp - 0.99, Ile - 0.84, Tyr - 0.97.

68. DArg-Arg-Pro-Hyp-Gly-Thi-Ser-DPhe-Thi-Arg-Ile-Tyr [(DArg$^0$Hyp$^3$Thi$^{5,8}$DPhe$^7$-BK)-Ile-Tyr]: k(415)=13.236 Arg - 3.07, Pro - 1.05, Gly - 1.07, Phe - 0.99, Ser - 0.96, Thi - 1.96, Hyp - 0.98, Ile - 0.96, Tyr - 0.97.

69. Arg-Pro-Pro-Gly-Phe-Ser-DPhe-Phe-Arg-DIle-Tyr [(DPhe$^7$-BK)-DIle-Tyr]: k(415)=0.639 Arg - 2.12, Pro - 2.13, Gly - 0.94, Phe - 3.16, Ser - 1.00, Ile - 0.77, Tyr - 0.88.

70. DArg-Arg-Pro-Pro-Gly-Phe-Ser-DPhe-Phe-Arg-DIle-Tyr [(DArg$^0$DPhe$^7$-BK)-DIle-Tyr]: k(415)=0.20 Arg - 2.86, Pro - 1.87, Gly - 1 01, Phe - 3.42, Ser - 0.71, Ile - 0.60, Tyr - 1.07.

71. Arg-Pro-Pro-Gly-Thi-Ser-DPhe-Thi-Arg-DIle-Tyr [(Thi$^{5,8}$DPhe$^7$-BK)-DIle-Tyr]: k(415)=0.515 Arg - 2.03, Pro - 1.95, Gly - 1.07, Phe - 1.07, Ser - 0.88, Thi - 1.91, Ile - 0.84, Tyr -1.09.

72. DArg-Arg-Pro-Pro-Gly-Thi-Ser-DPhe-Thi-Arg-DIle-Tyr [(DArg$^0$Thi$^{5,8}$DPhe$^7$-BK)-DIle-Tyr]: k(415)=0.205 Arg - 3.15, Pro -2.17, Gly - 0.99, Phe - 1.02, Ser - 1.00, Thi - 1.86, Ile - 0.83, Tyr - 1.02.

73. Arg-Pro-Hyp-Gly-Thi-Ser-DPhe-Thi-Arg-DIle-Tyr [(Hyp$^3$Thi$^{5,8}$ Phe$^7$-BK)-DIle-Tyr]: k(415)=0.429 Arg - 2.06, Pro - 1.13, Gly - 1.01, Phe 1.07, Ser - 0.90, Thi - 2.00, Ile - 0.89, Tyr - 1.03.

74. DArg-Arg-Pro-Hyp-Gly-Thi-Ser-DPhe-Thi-Arg-DIle-Tyr [(DArg$^0$Hyp$^3$Thi$^{5,8}$DPhe$^7$-BK)-DIle-Tyr]: k(415)=0.735 Arg - 3.28, Pro - 1.11, Gly - 1.10, Phe - 1.07, Ser - 0.90, Hyp - 0.80, Thi - 1.78, Ile - 0.85, Tyr - 1.11.

75. DNal-Pro-Pro-Gly-Thi-Ser-DPhe-Thi-Arg-DIle-Tyr [(DNal$^1$Thi$^{5,8}$DPhe$^7$-BK)-DIle-Tyr]: k(415)=10.111 Arg - 1.21, Pro - 1.75, Gly - 1.13, Phe - 1.19, Ser - 0.97, Thi- 1.79, Nal - 0.75, Ile - 0.90, Tyr - 1.3.

76. DArg-DNal-Pro-Pro-Gly-Thi-Ser-DPhe-Thi-Arg-DIle-Tyr [(DArg$^0$DNal$^1$Thi$^{5,8}$DPhe$^7$-BK)-DIle-Tyr]: k(415)=2.333 Arg - 2.07, Pro - 2.07, Gly - 1.04, Phe - 1.05, Ser - 0.86, Tyr - 0.96, Ile - 1.07, Nal - 1.02, Thi - 1.99.

77. DNal-Pro-Hyp-Gly-Thl-Ser-DPhe-Thi-Arg-DIle-Tyr [(DNal$^1$ Hyp$^3$Thi$^{5,8}$DPhe$^7$-BK)-DIle-Tyr]: k=Arg - 1.04, Pro - 1.01, Phe - 1.15, Ser - 0.98, Hyp - 0.98, Nal - 0.93, Thi - 1.84, Ile - 0.98, Tyr - 1.06.

78. DArg-DNal-Pro-Hyp-Gly-Thi-Ser-DPhe-Thi-Arg-DIle-Tyr [(DArg$^0$DNal$^1$Hyp$^3$Thi$^{5,8}$DPhe$^7$-BK)-DIle-Tyr]: k(415)=Arg - 2.11, Pro - 0.95, Gly - 1.00, Phe - 1.08, Ser - 0.99, Hyp - 1.01, Thi - 1.93, Tyr - 0.94, Ile - 0.95.

EXAMPLES OF BRADYKININ ANTAGONIST ACTIVITY

The bradykinin antagonists were assayed on isolated rat uterus in natural or induced estrus and on guinea pig ileum, according to the commonly accepted assay methods for bradykinin and related kinins as described by Trautschold (Handbook of Expt. Pharmacol. Vol 25, Springer Verlag, pp. 53–55, 1970) for inhibition of the myotropic activity of bradykinin. The inhibition potencies, as determined according to the commonly accepted manner described by Schild for antagonists of biologically active compounds (Br. J. Pharmacol. 2:189, 1947), and expressed as $pA_2$ values are determined on isolated rat uterus (RUT) and isolated guinea pig ileum (GPI). In the assays, a dose-response curve is determined for the reference substance bradykinin. The dose of bradykinin which produced a half maximal contraction of tissue is the $ED_{50}$ dose. An amount of bradykinin equivalent to twice the $ED_{50}$ dose is administered to the tissue 30 seconds after the start of incubation of the tissue with a dose of antagonist. Doses of antagonist are increased in this protocol until pre-incubation with a dose of antagonist reduces the contraction in response to the double $ED_{50}$ dose of bradykinin to response of a single $ED_{50}$ dose of bradykinin. The $pA_2$ value represents the negative logarithm of the molar concentration of antagonist necessary to reduce the response of a double $ED_{50}$ dose of bradykinin to that of an $ED_{50}$ dose. One unit of $pA_2$ value represents an order of magnitude change in potency. For comparison, the negative log of the dose of BK, the dose which causes half maximal contraction of the tissues, is commonly known as the $pD_2$ value. The $pD_2$ value for bradykinin is 7.9 on the rat uterus and 7.4 on the guinea pig ileum. The values for compounds of various Examples are reported in Table IV.

TABLE IV

BRADYKININ ANTAGONISM ON SMOOTH MUSCLES

| Example No. | Structure | $pA_2$/RUT | $pA_2$/GPI |
|---|---|---|---|
| 1. | DPhe$^7$—BK | | 5.0 |
| 2. | (CDF$^1$DPhe$^7$)—BK | 5.0(6) | 0 |
| 3. | (CDF$^1$Hyp$^3$DPhe$^7$)—BK | MIXED | 0 |
| 4. | DArg—(CDF$^1$DPhe$^7$)—BK | 5.4(8) | 0 |
| 5. | DArg—(CDF$^1$Hyp$^3$DPhe$^7$)—BK | 5.8(8) | 0 |
| 6. | (CDF$^1$DThi$^7$)—BK | I(2) | 0 |
| 7. | DArg—(CDF$^1$DThi$^7$)—BK | 0 | I(P) |
| 8. | (DArg$^1$Hyp$^3$Thi$^{5,8}$—DPhe$^7$)—BK | 5.4(6) | 5.4(2) |
| 9. | (DTyr$^1$Hyp$^3$DPhe$^7$)—BK | I | 0 |
| 10. | DArg—(DTyr$^1$Hyp$^3$DPhe$^7$)—BK | | I |
| 11. | (FDF$^1$Hyp$^3$DPhe$^7$)—BK | I | 0 |
| 12. | DArg—(FDF$^1$Hyp$^3$DPhe$^7$)—BK | 5.7(4) | 0 |
| 13. | (DTrp$^1$Hyp$^3$DPhe$^7$)—BK | | |
| 14. | DArg—(DTrp$^1$Hyp$^3$DPhe$^7$)—BK | | |
| 15. | (DVal$^1$Hyp$^3$DPhe$^7$)—BK | 0 | 0 |
| 16. | DArg—(DVal$^1$Hyp$^3$DPhe$^7$)—BK | I(P) | 0 |
| 17. | (DIle$^1$Hyp$^3$DPhe$^7$)—BK | I | 0 |
| 18. | DArg—(DIle$^1$Hyp$^3$DPhe$^7$)—BK | I | 0 |
| 19. | (DPhe$^1$Thi$^{5,8}$DPhe$^7$)—BK | 0 | 0 |
| 20. | (DThi$^1$Thi$^{5,8}$DPhe$^7$)—BK | 0 | 0 |
| 21. | (DPal$^1$Thi$^{5,8}$DPhe$^7$)—BK | 0 | 0 |
| 22. | (DNal$^1$Thi$^{5,8}$DPhe$^7$)—Bk | 5.6(8) | 0 |
| 23. | DArg—(DNal$^1$Thi$^{5,8}$DPhe$^7$)—BK | 5.8(6) | 0 |
| 24. | Lys—Lys—(DNal$^1$Thi$^{5,8}$DPhe$^7$)—BK | I(2X) | 0 |
| 25. | DNal—(DNal$^1$Thi$^{5,8}$DPhe$^7$)—BK | 5.6(6) | |
| 26. | (DNal$^1$Hyp$^{2,3}$Thi$^{5,8}$DPhe$^7$)—BK | 0 | 0 |
| 27. | DArg—(DNal$^1$Hyp$^{2,3}$Thi$^{5,8}$DPhe$^7$)—BK | 5.3(6) | 0 |
| 28. | Lys—Lys—(DNal$^1$Hyp$^{2,3}$Thi$^{5,8}$DPhe$^7$)—BK | 0 | 0 |
| 29. | (DNal$^1$DPhe$^7$)—Bk | 5.4(6) | 0 |
| 30. | (DNal$^1$Hyp$^3$DPhe$^7$)—Bk | 0 | 0.1% |
| 31. | DArg—(DNal$^1$DPhe$^7$)—BK | 5.6(5) | 0 |
| 32. | DArg—(DNal$^1$Hyp$^3$DPhe$^7$)—BK | 5.9(6) | 0 |
| 33. | (DThi$^1$DThi$^7$)—BK | 0 | 0 |
| 34. | (DThi$^1$Hyp$^3$DThi$^7$)—BK | 0 | I/0 |
| 35. | DArg—(DThi$^1$DThi$^7$)—BK | 0 | 0 |
| 36. | DArg—(DThi$^1$Hyp$^3$DThi$^7$)—BK | I/0 | 0 |
| 37. | (DNal$^1$DThi$^7$)—BK | 0 | 0 |
| 38. | (DNal$^1$Hyp$^3$DThi$^7$)—BK | 0 | 0 |
| 39. | DArg—(DNal$^1$DThi$^7$)—BK | 5.6(4) | 0 |
| 40. | DArg—(DNal$^1$Hyp$^3$DThi$^7$)—BK | 5.6(4) | 0 |
| 41. | (Thi$^{5,8}$DPhe$^7$DArg$^9$)—BK | 0.01% | 0 |
| 42. | Ac—(Thi$^{5,8}$DPhe$^7$DArg$^9$)—BK | 0 | 0 |
| 43. | DArg—(Thi$^{5,8}$DPhe$^7$DArg$^9$)—BK | 0 | 0 |
| 44. | Lys—Lys—(Thi$^{5,8}$DPhe$^7$DArg$^9$)—BK | 0 | 0 |
| 45. | (Hyp$^3$DPhe$^7$Phe$^9$)—BK | | |
| 46. | DArg—(Hyp$^3$DPhe$^7$Phe$^9$)—BK | | |
| 47. | (DNal$^1$Hyp$^3$DPhe$^7$Phe$^9$)—BK | | |
| 48. | DArg—(DNal$^1$Hyp$^3$DPhe$^7$Phe$^9$)—BK | | |
| 49. | (DArg$^1$Hyp$^3$DPhe$^7$Phe$^9$)—BK | | |
| 50. | DArg—(DArg$^1$Hyp$^3$DPhe$^7$Phe$^9$)—BK | | |
| 51. | (Thi$^{5,8}$DPhe$^7$)—BK—NH$_2$ | 0.02% | 0 |
| 52. | Ac—(Thi$^{5,8}$DPhe$^7$)—BK—NH$_2$ | 0 | 0 |
| 53. | DArg—(Thi$^{5,8}$DPhe$^7$)—BK—NH$_2$ | 0 | I/0 |
| 54. | Lys—Lys—(Thi$^{5,8}$DPhe$^7$)—BK—NH$_2$ | 0.02% | 0 |
| 55. | (Thi$^{5,8}$DPhe$^7$DArg$^9$)—BK—NH$_2$ | 0.01% | 0 |

TABLE IV-continued
BRADYKININ ANTAGONISM ON SMOOTH MUSCLES

| EXAMPLE No. | STRUCTURE | pA$_2$/RUT | pA$_2$/GPI |
|---|---|---|---|
| 56. | Ac(Thi$^{5,8}$DPhe$^7$DArg$^9$)—BK—NH$_2$ | 0 | 0 |
| 57. | DArg—(Thi$^{5,8}$DPhe$^7$DArg$^9$)—BK—NH$_2$ | 0.003% | 0 |
| 58. | Lys—Lys(Thi$^{5,8}$DPhe$^7$DArg$^9$)—BK—NH$_2$ | 0.02% | 0 |
| 59. | BK—Ile—Tyr | 26% | 21% |
| 60. | DArg—BK—Ile—Tyr | 25% | 34% |
| 61. | Lys—Lys—BK—Ile—Tyr | 18% | 21% |
| 62. | DLys—Lys—BK—Ile—Tyr | 5% | 1% |
| 63. | (DPhe$^7$)—BK—Ile—Tyr | 0.6% | MIXED |
| 64. | DArg—(DPhe$^7$)—BK—Ile—Tyr | 0.7% | 6.2(5) |
| 65. | (Thi$^{5,8}$DPhe$^7$)—BK—Ile—Tyr | 0.5% | MIXED |
| 66. | DArg—(Thi$^{5,8}$DPhe$^7$)—BK—Ile—Tyr | 0.3% | 5.8(5) |
| 67. | (Hyp$^3$Thi$^{5,8}$DPhe$^7$)—BK—Ile—Tyr | 0.06% | 0 |
| 68. | DArg—(Hyp$^3$Thi$^{5,8}$DPhe$^7$)—BK—Ile—Tyr | 0.02% | 6.7(5) |
| 69. | (DPhe$^7$)—BK—DIle—Tyr | 0 | 0 |
| 70. | DArg—(DPhe$^7$)—BK—DIle—Tyr | I/0 | 0 |
| 71. | (Thi$^{5,8}$DPhe$^7$)—BK—DIle—Tyr | 0 | 0 |
| 72. | DArg—(Thi$^{5,8}$DPhe$^7$)—BK—DIle—Tyr | 0 | 0 |
| 73. | (Hyp$^3$Thi$^{5,8}$DPhe$^7$)—BK—DIle—Tyr | 0.04% | 0 |
| 74. | DArg—(Hyp$^3$Thi$^{5,8}$DPhe$^7$)—BK—DIle—Tyr | 0 | 0 |
| 75. | (DNal$^1$Thi$^{5,8}$DPhe$^7$)—BK—DIle—Tyr | I | I |
| 76. | DArg—(DNal$^1$Thi$^{5,8}$DPhe$^7$)—BK—DIle—Tyr | 0 | 0 |
| 77. | (DNal$^1$Hyp$^3$Thi$^{5,8}$DPhe$^7$)—BK—DIle—Tyr | 0 | 0 |
| 78. | DArg—(DNal$^1$Hyp$^3$Thi$^{5,8}$DPhe$^7$)—BK—DIle—Tyr | 0 | 0 |

Biological activity is listed for the analogs on rat uterus (RUT), guinea pig ileum (GPI). Agonist potency is listed as percent of BK potency. Antagonist potency is listed as the pA$_2$ value and is underlined, followed in parenthese by the number of tissues in the determination. I(#) indicates antagonism in # determination without quantitation. I/0 indicates analog exhibits both antagonism and no effect on separate tissues in screening assays. MIXED indicates a mixed agonist/antigonist analog. I(P) indicates partial antagonism.

EXAMPLE OF THE ANTAGONISM OF BRADYKININ ANTAGONISTS ON RAT BLOOD PRESSURE

The in vivo effects of bradykinin antagonists on blood pressure in the anesthetized rat are determined according to the assay described by Roblero, Ryan and Stewart (Res. Commun. Pathol. Pharmacol. 6:207, 1973). The antagonists also produce inhibition of the bradykinin response when injected as a bolus admixture of bradykinin plus antagonist by either the ia or iv route of administration. The results of tests on compounds of the various examples are - reported in Table V.

TABLE V
BRADYKININ ANTAGONISM ON BLOOD PRESSURE

| EXAMPLE NO | STRUCTURE | RBP-IA | RBP-IV | % DESTR |
|---|---|---|---|---|
| 1. | DPhe$^7$—BK | | | |
| 2. | (CDF$^1$DPhe$^7$)—BK | I(B) | I(B) | — |
| 3. | (CDF$^1$Hyp$^3$DPhe$^7$)—BK | I(P) | I(P) | — |
| 4. | DArg—(CDF$^1$DPhe$^7$)—BK | I(P) | I(P) | — |
| 5. | DArg—(CDF$^1$Hyp$^3$DPhe$^7$)—BK | I(P) | I(P) | — |
| 6. | (CDF$^1$DThi$^7$)—BK | 0 | 0 | — |
| 7. | DArg—(CDF$^1$DThi$^7$)—BK | 0 | 0 | — |
| 8. | (DArg$^1$Hyp$^3$Thi$^{5,8}$DPhe$^7$)—BK | I(B) | I(B) | — |
| 9. | (DTyr$^1$Hyp$^3$DPhe$^7$)—BK | I(B) | I(B) | — |
| 10. | DArg—(DTyr$^1$Hyp$^3$DPhe$^7$)—BK | I(B) | I(B) | — |
| 11. | (FDF$^1$Hyp$^3$DPhe$^7$)—BK | I(B) | I(B) | — |
| 12. | DArg—(FDF$^1$Hyp$^3$DPhe$^7$)—BK | I(B) | I(B) | — |
| 13. | (DTrp$^1$Hyp$^3$DPhe$^7$)—BK | | | |
| 14. | DArg—(DTrp$^1$Hyp$^3$DPhe$^7$)—BK | | | |
| 15. | (DVal$^1$Hyp$^3$DPhe$^7$)—BK | 0 | 0 | — |
| 16. | DArg—(DVal$^1$Hyp$^3$DPhe$^7$)—BK | 0 | 0 | — |
| 17. | (DIle$^1$Hyp$^3$DPhe$^7$)—BK | 0 | 0 | — |
| 18. | DArg—(DIle$^1$Hyp$^3$DPhe$^7$)—BK | 0 | 0 | — |
| 19. | (DPhe$^1$Thi$^{5,8}$DPhe$^7$)—BK | I(B) | I(B) | — |
| 20. | (DThi$^1$Thi$^{5,8}$DPhe$^7$)—BK | 0 | 0 | — |
| 21. | (DPal$^1$Thi$^{5,8}$DPhe$^7$)—BK | 0 | 0 | — |
| 22. | (DNal$^1$Thi$^{5,8}$DPhe$^7$)—BK | I(B) | I(B) | — |
| 23. | DArg—(DNal$^1$Thi$^{5,8}$DPhe$^7$)—BK | I(B) | I(B) | — |
| 24. | Lys—Lys—(DNal$^1$Thi$^{5,8}$DPhe$^7$)—BK | I(B) | I(B) | — |
| 25. | DNal—(DNal$^1$Thi$^{5,8}$DPhe$^7$)—BK | | | |
| 26. | (DNal$^1$Hyp$^{2,3}$Thi$^{5,8}$DPhe$^7$)—BK | I(B) | I(B) | — |
| 27. | DArg—(DNal$^1$Hyp$^{2,3}$Thi$^{5,8}$DPhe$^7$)—BK | I(B) | I(B) | — |
| 28. | Lys—Lys—(DNal$^1$Hyp$^{2,3}$Thi$^{5,8}$DPhe$^7$)—BK | I(B) | I(B) | — |
| 29. | (DNal$^1$DPhe$^7$)—BK | I(B) | I(B) | — |
| 30. | (DNal$^1$Hyp$^3$DPhe$^7$)—BK | 0 | 0 | — |
| 31. | DArg—(DNal$^1$DPhe$^7$)—BK | I(B) | I(B) | — |

TABLE V-continued
BRADYKININ ANTAGONISM ON BLOOD PRESSURE

| EXAMPLE NO | STRUCTURE | RBP-IA | RBP-IV | % DESTR |
|---|---|---|---|---|
| 32. | DArg—(DNal$^1$Hyp$^3$DPhe$^7$)—BK | I(B) | I(B) | — |
| 33. | (DThi$^1$DThi$^7$)—BK | 0 | 0 | — |
| 34. | (DThi$^1$Hyp$^3$DThi$^7$)—BK | I(B) | I(B) | — |
| 35. | DArg—(DThi$^1$DThi$^7$)—BK | 0 | 0 | — |
| 36. | DArg—(DThi$^1$Hyp$^3$DThi$^7$)—BK | I(B) | I(B) | — |
| 37. | (DNal$^1$DThi$^7$)—BK | I(B) | I(B) | — |
| 38. | (DNal$^1$Hyp$^3$DThi$^7$)—BK | I(B) | I(B) | — |
| 39. | DArg—(DNal$^1$DThi$^7$)—BK | 0 | 0 | — |
| 40. | DArg—(DNal$^1$Hyp$^3$DThi$^7$)—BK | I(B) | I(B) | — |
| 41. | (Thi$^{5,8}$DPhe$^7$DArg$^9$)—BK | 0.1% | 0.6% | 77% |
| 42. | Ac—(Thi$^{5,8}$DPhe$^7$DArg$^9$)—BK | 0 | 0 | — |
| 43. | DArg—(Thi$^{5,8}$DPhe$^7$DArg$^9$)—BK | I(B) | I(B) | — |
| 44. | Lys—Lys—(Thi$^{5,8}$DPhe$^7$DArg$^9$)—BK | 0.2% | 14% | 0 |
| 45. | (Hyp$^3$DPhe$^7$Phe$^9$)—BK | 0 | 0 | — |
| 46. | DArg—(Hyp$^3$DPhe$^7$Phe$^9$)—BK | I(B) | I(B) | — |
| 47. | (DNal$^1$—Hyp$^3$—DPhe$^7$—Phe$^9$)—BK | | | |
| 48. | DArg—(DNal$^1$Hyp$^3$DPhe$^7$Phe$^9$)—BK | | | |
| 49. | (DArg$^1$Hyp$^3$DPhe$^7$Phe$^9$)—BK | 0 | 0 | — |
| 50. | DArg—(DArg$^1$Hyp$^3$DPhe$^7$Phe$^9$)—BK | I(B) | I(B) | — |
| 51. | (Thi$^{5,8}$DPhe$^7$)—BK—NH$_2$ | 0.05% | 2% | 52% |
| 52. | Ac—(Thi$^{5,8}$DPhe$^7$)—BK—NH$_2$ | I(B) | I(B) | — |
| 53. | DArg—(Thi$^{5,8}$DPhe$^7$)—BK—NH$_2$ | 0 | I(P) | — |
| 54. | Lys—Lys—(Thi$^{5,8}$DPhe$^7$)—BK—NH$_2$ | | (long duration depressor) | |
| 55. | (Thi$^{5,8}$DPhe$^7$DArg$^9$)—BK—NH$_2$ | 0.1% | 0.9% | 61% |
| 56. | Ac(Thi$^{5,8}$DPhe$^7$DArg$^9$)—BK—NH$_2$ | I(B) | I(B) | — |
| 57. | DArg—(Thi$^{5,8}$DPhe$^7$DArg$^9$)—BK—NH$_2$ | I(B) | I(B) | — |
| 58. | Lys—Lys(Thi$^{5,8}$DPhe$^7$DArg$^9$)—BK—NH$_2$ | 0.2% | 3% | 60% |
| 59. | BK—Ile—Tyr | 6% | 103% | 61% |
| 60. | DArg—BK—Ile—Tyr | 12% | 189% | 47% |
| 61. | Lys—Lys—BK—Ile—Tyr | 9% | 497% | 0 |
| 62. | DLys—Lys—BK—Ile—Tyr | 5% | 165% | 0 |
| 63. | (DPhe$^7$)—BK—Ile—Tyr | 0.2% | 2% | 70% |
| 64. | DArg—(DPhe$^7$)—BK—Ile—Tyr | 0 | 0 | — |
| 65. | (Thi$^{5,8}$DPhe$^7$)—BK—Ile—Tyr | 0.06% | 6% | 0 |
| 66. | DArg—(Thi$^{5,8}$DPhe$^7$)—BK—Ile—Tyr | I(B) | I(B) | — |
| 67. | (Hyp$^3$Thi$^{5,8}$DPhe$^7$)—BK—Ile—Tyr | 0 | 0 | — |
| 68. | DArg—(Hyp$^3$Thi$^{5,8}$DPhe$^7$)—BK—Ile—Tyr | 7% | AG | — |
| 69. | (DPhe$^7$)—BK—DIle—Tyr | 0.3% | 2% | 75% |
| 70. | DArg—(DPhe$^7$)—BK—DIle—Tyr | 0 | 0 | — |
| 71. | (Thi$^{5,8}$DPhe$^7$)—BK—DIle—Tyr | 0.2% | 2% | 55% |
| 72. | DArg—(Thi$^{5,8}$DPhe$^7$)—BK—DIle—Tyr | 0 | 0 | — |
| 73. | (Hyp$^3$Thi$^{5,8}$DPhe$^7$)—BK—DIle—Tyr | 0 | 0 | — |
| 74. | DArg—(Hyp$^3$Thi$^{5,8}$DPhe$^7$)—BK—DIle—Tyr | I(B) | I(B) | — |
| 75. | (DNal$^1$Thi$^{5,8}$DPhe$^7$)—BK—DIle—Tyr | | | |
| 76. | DArg—(DNal$^1$Thi$^{5,8}$DPhe$^7$)—BK—DIle—Tyr | 0 | 0 | — |
| 77. | (DNal$^1$Hyp$^3$Thi$^{5,8}$DPhe$^7$)—BK—DIle—Tyr | | | |
| 78. | DArg—(DNal$^1$Hyp$^3$Thi$^{5,8}$DPhe$^7$)—BK—DIle—Tyr | I(P) | I(P) | — |

Biological activity is listed for the analogs on rat blood pressure (RBP) following intra-aortic (IA) and intravenous (IV) bolus administration. % DESTR indicates metabolic breakdown of BK-like agonists in RBP assay relative to BK = 100%. Agonist potency is listed as percent of BK potency. I(B) indicates antagonism of BK-induced depressor effect. MIXED indicates a mixed agonist/antagonist analog. AG indicates agonist activity. I(P) indicates BK antagonist activity as well as pressor activity.

Therapeutic applications of the novel bradykinin antagonists include not only treatment for the production of bradykinin or related kinins by the animal but also the injection of bradykinin related peptides into an animal as a result of bites and stings or injection similarly of enzymes which cause production of bradykinin. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic, inflammatory or pathological conditions which are known to be mediated by bradykinin or exacerbated by an overproduction of bradykinin can also be achieved. These conditions include local trauma such as wounds, burns and rashes, angina, arthritis, asthma, allergies, rhinitis, shock, inflammatory bowel disease, low blood pressure, systemic treatment of pain and inflammation. The present bradykinin antagonists, as discussed, may be advantageously administered in a variety of ways including sublingual absorption as with nitroglycerine or patch administration using agents for assisting absorption through the skin such as for the treatment of angina. Based upon the PA$_2$ and ED$_{50}$ data disclosed in this invention and in the prior art related to agonist potency, it is possible for one skilled in the art to make a determination of the dosage of the novel bradykinin antagonists of the invention.

It is therefore estimated that the dosage range for typical application in such conditions as the pain and inflammation of wounds, burns and rashes would be 0.1–5 mg/ml; for a nasal spray formulation suitable for treating rhinitis, allergies and asthma suitable dosage range would be 0.1–5 mg/ml; for intravenous formulation suitable for the treatment of systemic inflammation, shock, arthritis, allergies, asthma; for an oral formulation for the treatment of inflammatory bowel disease or general pain and inflammation a suitable dosage range would be 10–100 mg/kg. Bradykinin antagonists can also be administered intravaginally, intrarectally, intrabuccally or by any other accepted internal application.

The active ingredients of the invention as heretofore discussed may be administered topically, subcutaneously, sublingually, intravenously or may be applied in the form of suppositories or sprays in a solution or medium of a pharmaceutically acceptable carrier and sterile vehicles as are known by those skilled in the art. The pharmaceutical preparations can be combined with acceptable solid or liquid excipients suitable for topical applications in the way of ointments and creams or may be combined with liquid excipients to form aerosols and sprays in formats well known to those skilled in the art. Pharmaceutical preparations in accordance with the invention may also utilize a suitable carrier for intravenous and subcutaneous administration employing various solutions or serums as is known by those skilled in the art as well as sublingual formulations utilizing pharmaceutically acceptable carriers such as syrups, gels or solid tablets containing well known pharmaceutical excipients.

As will be recognized by those skilled in the art the present invention has a wide range of applicability to providing competitive inhibitors to the biological activities of bradykinin produced by the body in illness, injury and shock. The advantages of the invention in substituting the L-Pro position 7 with amino acids of the D-configuration to convert bradykinin agonists to antagonists provide a wide variety of specific and competitive antagonists for reducing the known effects of bradykinin. The additional advantages of the invention of modifying the L-Pro position 7 in conjunction with modifications at the other positions of the novel bradykinin antagonists provides a variety of useful compounds. It will further be appreciated that the present invention is susceptible to these and other modifications within the parameters of the invention without departing from the scope of the following claims.

What is claimed is:

1. The peptide having the formula

CDF-Pro-Pro-Gly-Phe-Ser-DPhe-Phe-Arg.

2. The peptide having the formula

DArg-CDF-Pro-Hyp-Gly-Phe-Ser-DPhe-DPhe-Arg.

3. The peptide having the formula

DArg-FDF-Pro-Hyp-Gly-Thi-Ser-DPhe-Phe-Arg.

4. The peptide having the formula

DArg-Arg-Pro-Pro-Gly-Thi-Ser-DPhe-Thi-Phe-Ile-Tyr.

5. The peptide having the formula

Ac-Arg-Pro-Pro-Gly-Thi-Ser-DPhe-Thi-Phe-Ile-Tyr.

6. The peptide having the formula

DArg-DArg-Pro-Hyp-Gly-Phe-Ser-DPhe-Phe-Phe.

* * * * *